US00PP35163P2

(12) United States Plant Patent
Carrella

(10) Patent No.: US PP35,163 P2
(45) Date of Patent: May 9, 2023

(54) ***CALIBRACHOA* PLANT NAMED 'KLECA22491'**

(50) Latin Name: ***Calibrachoa* sp.**
Varietal Denomination: KLECA22491

(71) Applicant: KLEMM + SOHN GMBH & CO. KG, Stuttgart (DE)

(72) Inventor: Angelo Carrella, Palma Campania (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/829,624

(22) Filed: Jun. 1, 2022

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 5/02
See application file for complete search history.

(56) References Cited

PUBLICATIONS https://online.flippingbook.com/view/114377057/126/; Mast Young Plants 2021/2022 Spring Catalog; 2021; 5 pages.*
https://www.selectanorthamerica.com/springplants/seriesinfo/?phid=066007160005863; Aug. 24, 2022; 1 page.*

* cited by examiner

*Primary Examiner* — Kent L Bell
(74) *Attorney, Agent, or Firm* — Weatherly IP Solutions, LLC; James M. Weatherly

(57) ABSTRACT

A new *Calibrachoa* plant particularly distinguished by having a large white single flowers with a semi-trailing habit, is disclosed.

1 Drawing Sheet

Genus and species: *Calibrachoa* sp.
Variety denomination: 'KLECA22491'.

BACKGROUND OF THE NEW PLANT

The present invention comprises a new and distinct variety of *Calibrachoa*, botanically known as *Calibrachoa* sp, and hereinafter referred to by the variety name 'KLECA22491'. 'KLECA22491' originated from a controlled-cross between the proprietary female *Calibrachoa* variety 'KLECA12235' (U.S. Plant Pat. No. 25,287) and the male *Calibrachoa* variety 'KLECA17002' (unpatented).

In August 2015, two *Calibrachoa* parental lines, the female variety 'KLECA12235' and the male variety 'KLECA17002' were crossed via a controlled cross in Stuttgart, Germany and seeds were obtained. The seeds were sown and plants were grown for evaluation. A single plant was selected in May 2016 and subsequently named 'KLECA22491'. In June 2016, 'KLECA22491' was first vegetatively propagated by cuttings. 'KLECA22491' was found to reproduce true to type in successive generations of asexual propagation via cuttings.

SUMMARY

The following are the most outstanding and distinguishing characteristics of this new variety when grown under normal horticultural practices in Stuttgart, Germany.

1. Large, single white flowers; and
2. Semi-trailing plant habit.

DESCRIPTION OF THE PHOTOGRAPH

This new *Calibrachoa* plant is illustrated by the accompanying photograph which shows a close-up of the whole plant. The photograph is of a 10-week-old-plant grown in in Stuttgart, Germany in May 2019. The colors shown are as true as can be reasonably obtained by conventional photographic procedures.

DESCRIPTION OF THE NEW VARIETY

The following detailed descriptions set forth the distinctive characteristics of 'KLECA22491'. The data which define these characteristics were collected from asexual reproductions carried out in Stuttgart, Germany. Data was collected on 8-week old plants after transplant in Stuttgart, Germany May 2022. Color references are to The R.H.S. Colour Chart of The Royal Horticultural Society of London (R.H.S.), 5$^{th}$ edition (2007).

Classification:
- *Family.*—Solanaceae.
- *Species.*—*Calibrachoa* sp.
- *Common name.*—*Calibrachoa.*

Parentage:
- *Female.*—*Calibrachoa* line 'KLECA12235'(U.S. Plant Pat. No. 25,287).
- *Male.*—*Calibrachoa* line 'KLECA17002' (unpatented).

Plant description:
- *Life cycle.*—Annual.
- *Form.*—Short lived sub shrub.
- *Habit.*—Semi-trailing.
- *Height (from soil line to top of foliage).*—12.0 cm.
- *Spread.*—31.0 cm.

Propagation:
*Type cuttings*.—Tip cuttings.
*Time to produce a rooted cutting*.—3 weeks.
*Plant flowering season*.—Spring to October.
Stems:
*Stem color*.—RHS 143C.
*Pubescence*.—Yes.
*Pubescence color*.—RHS 155A.
*Stem diameter*.—0.1 cm.
*Stem length*.—13.1 cm. From soil line to first node: 0.5 cm.
*Internode length*.—2.6 cm.
Leaves:
*Arrangement*.—Alternate or opposite.
*Shape*.—Lanceolate.
*Apex*.—Obtuse.
*Base*.—Obtuse.
*Margin*.—Ciliate.
*Surface* (*both upper and lower*).—Pubescent.
*Surface pubescence*.—Present.
*Pubescent color*.—RHS 155A.
*Venation*.—Pinnate.
*Venation color*.—Upper surface: RHS 137C. Lower surface: RHS 138B.
*Length*.—3.3 cm.
*Width*.—0.8 cm.
*Color*.—Upper surface: RHS 137C. Lower surface: RHS 138B.
*Fragrance*.—Absent.
Flowers:
*Flowering habit*.—Single.
*Flower type*.—Single.
*Flowering requirements*.—A minimum amount of sunlight is required.
*Duration of flowers*.—7 days.
*Corolla texture*.—Smooth.
*Shape*.—Funnel-shaped.
*Fragrance*.—Absent.
*Number of flowers per plant*.—More than 50 flowers.
Flower buds (before opening):
*Surface*.—Pubescent.
*Length*.—2.4 cm.
*Diameter*.—0.5 cm.
*Shape*.—Irregular to oblong.
*Color*.—RHS 157A.
*Typical number per plant*.—25 to 35 in the flowering time.
Petiole:
*Length*.—2 cm.
*Diameter*.—0.1 cm.
Peduncle:
*Length*.—2.0 cm.
*Diameter*.—0.1 cm.
*Color*.—RHS 144A.
*Texture*.—Pubescent.
*Anthocyanin color*.—Absent.
Flower description:
*Flower depth*.—2.4 cm.
*Flower tube length*.—1.8 cm.
*Flower tube diameter*.—1.0 cm.
*Flower diameter*.—3.7 cm.
*Flower throat diameter*.—1.2 cm.
*Pedicel color*.—RHS 144A.
*Pedicel length*.—1.8 cm to 2.2 cm.
*Calyx*.—RHS 137B.
Sepals:
*Quantity*.—5.
*Shape*.—Obtuse.
*Texture*.—Pubescent.
*Apex*.—Obtuse.
*Margin*.—Ciliate.
*Length*.—1.3 cm.
*Diameter*.—0.2 cm.
*Sepal color*.—Upper surface: RHS 137B. Lower surface: RHS 146B.
Petals:
*Shape*.—Obcordate.
*Quantity*.—5.
*Length*.—1.6 cm.
*Apex*.—Obtuse.
*Margin*.—Entire.
*Base*.—Fused into the tube.
*Pubescence*.—Absent.
*Lobe length*.—1.6 cm.
*Lobe width*.—1.4 cm.
*Color*.—Lobe color: Upper surface: RHS NN155D. Lower surface: RHS NN155D. Corolla tube color: Inner: RHS 3C. Outer: RHS 1D.
*Fragrance*.—Absent.
Reproductive organs:
*Stamen number*.—5.
*Stamen color*.—Anther color: RHS 13A. Anther length: Less than 0.1. Filament length: 0.7 cm. Filament color: RHS 157C. Pollen amount: Medium to abundant. Pollen color: RHS 8B.
*Ovary*.—Placenta arrangement: Ovate. Pistil number: 1. Pistil length: 0.9 cm. Stigma color: RHS 145B. Stigma shape: Discoid. Style length: 0.8 cm. Style color: RHS 1545C.
Fruit/seed set: None observed.
Disease/insect resistance: No pests and disease were observed.

COMPARISON WITH PARENTAL LINES AND KNOWN VARIETY

'KLECA22491' is distinguished from its parents as described in Table 1:

TABLE 1

Comparison with Parental Lines

| Trait | Variety 'KLECA22491' | Female parent 'KLECA12235' | Male Parent 'KLECA17002' |
|---|---|---|---|
| Flower Size | Bigger flower size than the parents | Smaller flower size than KLECA22491 | Smaller flower size than KLECA22491 |
| Habit | Semi-Trailing | Trailing | Mounding |

'KLECA22491' is most similar to the *Calibrachoa* plant named 'KLECA17395' (not patented). Differences between the two varieties are described in Table 2:

TABLE 2

Comparison with Similar Variety

| Trait | Variety 'KLECA22491' | Commercial line 'KLECA17395' |
|---|---|---|
| Flower size | Bigger flower size | Smaller flower size |

I claim:

1. A new and distinct cultivar of *Calibrachoa* Plant Named 'KLECA22491' as described and illustrated herein.

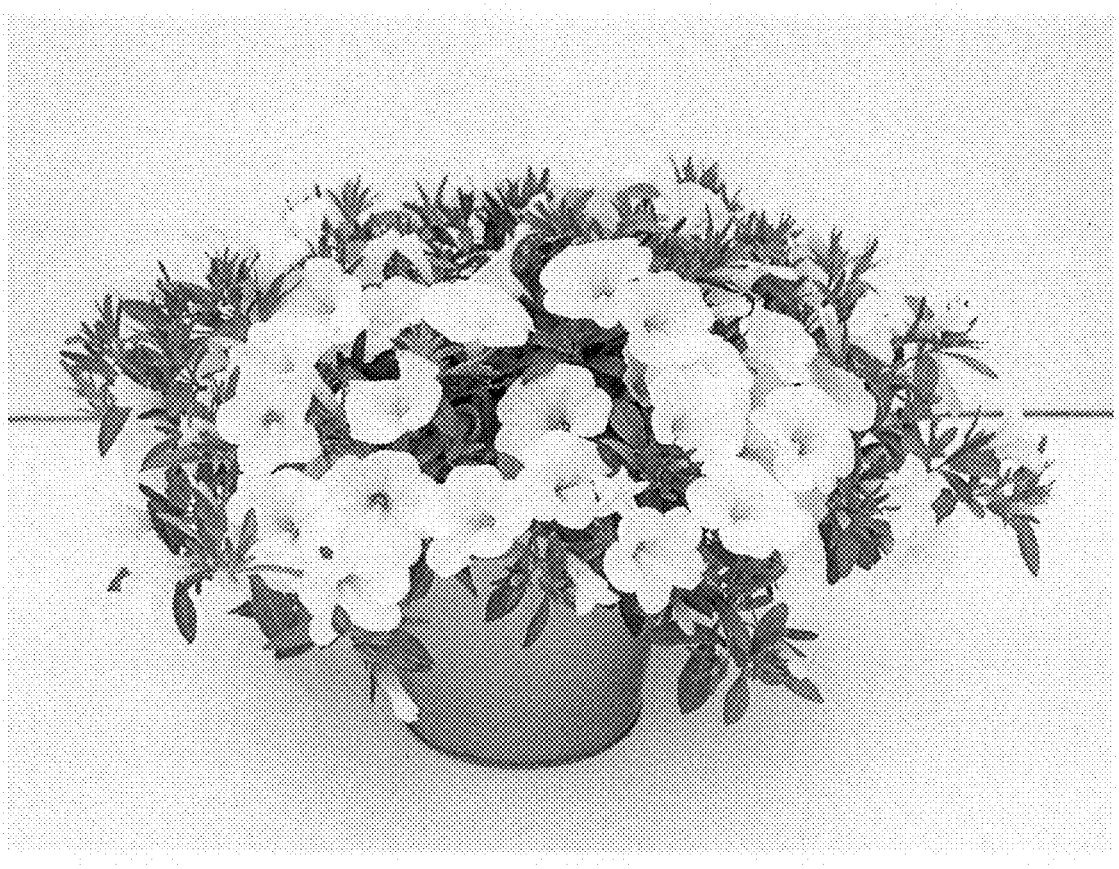

* * * * *